US010588669B2

(12) United States Patent
Pham et al.

(10) Patent No.: US 10,588,669 B2
(45) Date of Patent: Mar. 17, 2020

(54) TRANS-ILIAC CONNECTOR

(71) Applicant: GLOBUS MEDICAL, INC., Audubon, PA (US)

(72) Inventors: Khiem Pham, Chalfont, PA (US); Andrew Iott, Newtown Square, PA (US); Brad Juchno, Yardley, PA (US); Douglas Cahill, Lititz, PA (US)

(73) Assignee: Globus Medical, Inc., Audubon, PA (US)

( * ) Notice: Subject to any disclaimer, the term of this patent is extended or adjusted under 35 U.S.C. 154(b) by 133 days.

(21) Appl. No.: 15/787,019

(22) Filed: Oct. 18, 2017

(65) Prior Publication Data
US 2018/0036041 A1   Feb. 8, 2018

Related U.S. Application Data

(63) Continuation of application No. 12/902,789, filed on Oct. 12, 2010, now Pat. No. 9,814,493.

(60) Provisional application No. 61/250,738, filed on Oct. 12, 2009.

(51) Int. Cl.
*A61B 17/70*   (2006.01)

(52) U.S. Cl.
CPC ........ *A61B 17/7052* (2013.01); *A61B 17/705* (2013.01)

(58) Field of Classification Search
CPC .. A61B 17/7049–4052; A61B 17/7055; A61B 17/7011; A61B 17/7014; A61B 17/7041; A61B 17/7043
See application file for complete search history.

(56) References Cited

U.S. PATENT DOCUMENTS

| | | | | |
|---|---|---|---|---|
| 5,000,166 A * | 3/1991 | Karpf | ..................... | A61B 17/70 606/250 |
| 5,490,851 A * | 2/1996 | Nenov | ............... | A61B 17/7055 606/252 |
| 5,498,262 A * | 3/1996 | Bryan | ................ | A61B 17/1757 606/250 |
| 5,643,260 A * | 7/1997 | Doherty | ............. | A61B 17/7001 606/270 |
| 5,667,506 A * | 9/1997 | Sutterlin | ............ | A61B 17/7055 606/252 |
| 5,947,965 A * | 9/1999 | Bryan | ................ | A61B 17/1757 606/250 |
| 6,238,396 B1 * | 5/2001 | Lombardo | ......... | A61B 17/7052 606/251 |
| 6,379,354 B1 * | 4/2002 | Rogozinski | ........ | A61B 17/6416 606/260 |
| 6,419,703 B1 * | 7/2002 | Fallin | ..................... | A61F 2/4405 623/17.11 |
| 6,669,697 B1 * | 12/2003 | Pisharodi | ........... | A61B 17/7007 606/250 |
| 6,716,213 B2 * | 4/2004 | Shitoto | ............. | A61B 17/7035 606/264 |

(Continued)

*Primary Examiner* — Jacqueline T Johanas

(57) ABSTRACT

A spine stabilization implant includes a first portion having a first fixed angulated extension, a first rod receiving element and a connecting element. The implant also includes a second portion having a second fixed angulated extension, a second rod receiving element, and a receiving portion for receiving the connecting element of the first portion. The second portion is configured with a locking assembly for locking the first portion and second portion to one another.

11 Claims, 5 Drawing Sheets

(56) References Cited

U.S. PATENT DOCUMENTS

| | | | |
|---|---|---|---|
| RE39,325 E * | 10/2006 | Bryan | 606/86 A |
| 7,220,262 B1 * | 5/2007 | Hynes | A61B 17/7011 606/279 |
| 7,294,129 B2 * | 11/2007 | Hawkins | A61B 17/7037 606/86 A |
| 9,510,872 B2 * | 12/2016 | Donner | A61B 17/7026 |
| 9,603,634 B1 * | 3/2017 | Frankel | A61B 17/7049 |
| 9,814,493 B2 * | 11/2017 | Pham | A61B 17/7052 |
| 2003/0060823 A1 * | 3/2003 | Bryan | A61B 17/7011 606/86 A |
| 2004/0116928 A1 * | 6/2004 | Young | A61B 17/7052 606/253 |
| 2006/0025769 A1 * | 2/2006 | Dick | A61B 17/7035 606/86 A |
| 2006/0200130 A1 * | 9/2006 | Hawkins | A61B 17/7037 606/86 A |
| 2006/0217710 A1 * | 9/2006 | Abdou | A61B 17/6433 606/54 |
| 2007/0276374 A1 * | 11/2007 | Broman | A61B 17/7011 606/308 |
| 2008/0021454 A1 * | 1/2008 | Chao | A61B 17/7044 606/250 |
| 2008/0021455 A1 * | 1/2008 | Chao | A61B 17/7034 606/250 |
| 2008/0021456 A1 * | 1/2008 | Gupta | A61B 17/7049 606/250 |
| 2008/0051783 A1 * | 2/2008 | Null | A61B 17/7055 606/261 |
| 2008/0154306 A1 * | 6/2008 | Heinz | A61B 17/7055 606/256 |
| 2009/0182376 A1 * | 7/2009 | Iott | A61B 17/7052 606/246 |
| 2009/0216276 A1 * | 8/2009 | Pasquet | A61B 17/7043 606/249 |
| 2009/0249851 A1 * | 10/2009 | Isaacs | A61B 17/7011 72/31.04 |
| 2009/0270920 A1 * | 10/2009 | Douget | A61B 17/7055 606/254 |
| 2009/0299411 A1 * | 12/2009 | Laskowitz | A61B 17/7008 606/246 |
| 2010/0049252 A1 * | 2/2010 | Smisson, III | A61B 17/7043 606/250 |
| 2010/0222825 A1 * | 9/2010 | Paul | A61B 17/7044 606/280 |
| 2011/0087289 A1 * | 4/2011 | Pham | A61B 17/7052 606/250 |
| 2012/0101533 A1 * | 4/2012 | Purcell | A61B 17/7037 606/305 |
| 2013/0053854 A1 * | 2/2013 | Schoenefeld | A61B 17/1757 606/87 |
| 2013/0172936 A1 * | 7/2013 | Berrevoets | A61B 17/7055 606/278 |
| 2014/0296917 A1 * | 10/2014 | Donner | A61B 17/7026 606/248 |
| 2015/0289913 A1 * | 10/2015 | Vaidya | A61B 17/8066 623/22.12 |
| 2016/0135846 A1 * | 5/2016 | Mirda | A61B 17/7004 606/267 |
| 2017/0325849 A1 * | 11/2017 | Gleason | A61B 17/7052 |
| 2018/0008321 A1 * | 1/2018 | Stern | A61B 17/7002 |

\* cited by examiner

TRANS-ILIAC CONNECTOR

CROSS-REFERENCE TO RELATED APPLICATIONS

The present application is a non-provisional application which is a continuation application of U.S. patent application Ser. No. 12/902,789 filed on Oct. 12, 2010, which claims the benefit of priority of U.S. Provisional Application Ser. No. 61/250,738 filed on Oct. 12, 2009, the entire contents of which is hereby expressly incorporated by reference into this disclosure as if set forth fully herein.

FIELD OF THE INVENTION

The present invention relates to a spinal implant that stabilizes and supports the spine.

BACKGROUND OF THE INVENTION

Spinal deformities, spinal injuries, and other spinal conditions may be treated with the use of spinal implants. Spinal implants are designed to support the spine and properly position the components of the spine. One such spinal implant includes an elongated rod and a plurality of bone anchors. The elongated rod is positioned to extend along one or more of the components of the spine and the bone anchors are attached to the spinal components at one end and secured to the elongated rod at the other end. There is a need for a spinal implant that enables fusion and stability of the spine at the iliac portion of the spine.

BRIEF DESCRIPTION OF THE DRAWINGS

The invention will be more readily understood with reference to the embodiments thereof illustrated in the attached drawing figures, in which.

SUMMARY OF THE INVENTION

A spine stabilization implant includes a first portion having a first fixed angulated extension, a first rod receiving element and a connecting element. The implant also includes a second portion having a second fixed angulated extension, a second rod receiving element, and a receiving portion for receiving the connecting element of the first portion. The second portion is configured with a locking assembly for locking the first portion and second portion to one another.

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
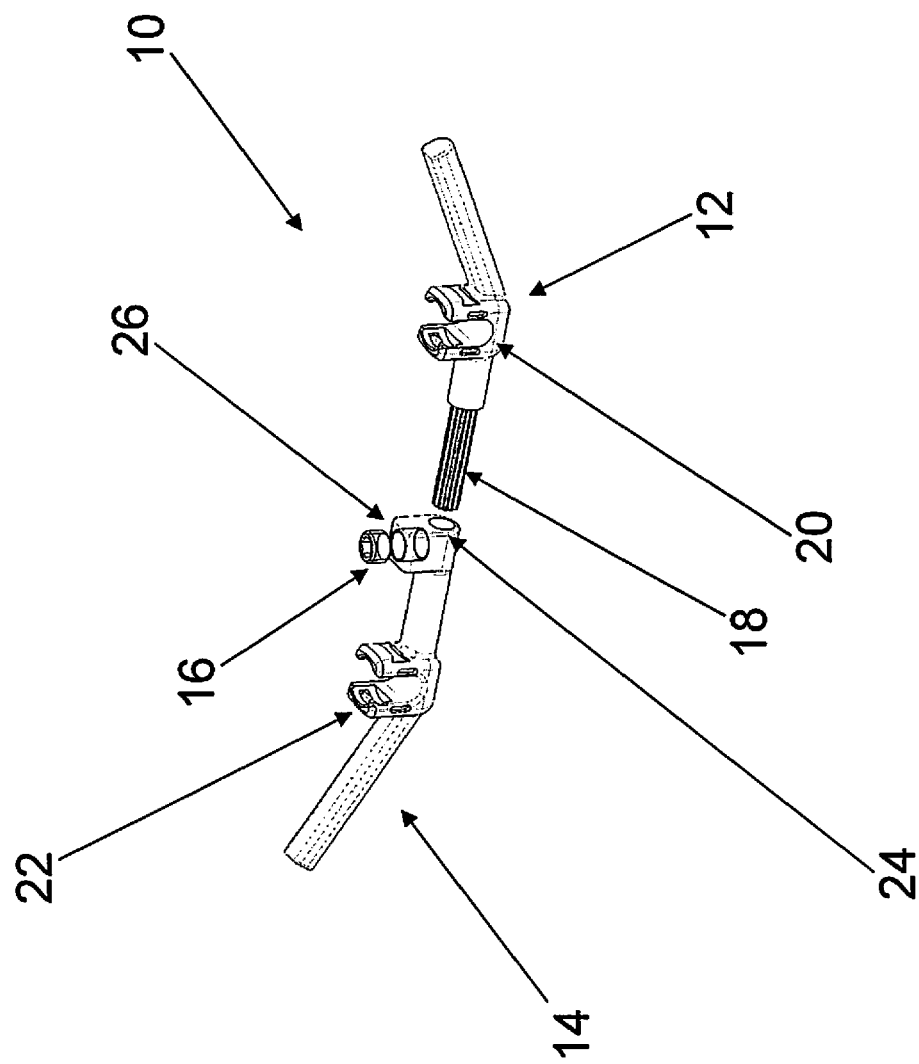
FIG. 1 illustrates the iliac connector according to one embodiment of the present invention.

FIG. 1 illustrates a trans-iliac connector 10 according to one embodiment of the present invention. The connector 10 is configured and dimensioned to span the iliac crest medial/laterally. More specifically, the connector 10 includes a male portion 12 and a female portion 14. The male portion 12 of the connector 10 is received into the female portion 14 of the connector 10 and locked into placed using a set screw 16. The male portion 12 is configured with an extension 18 and can be rotated and adjusted translationally depending on the anatomy of the patient. In one embodiment, the male portion 12 may pivot in any direction with respect to the female portion 14 of the connector. The male portion 12 also includes a portion which extends distally in a fixed angle with respect to the extension 18. The male portion 12 also includes a rod receiving element 20 for receiving an elongated rod. The rod receiving element 20 is configured and adapted to capture and retain an elongated rod. The rod receiving element 20 is designed and configured to receive a locking cap which secures the elongated rod within the rod receiving element 20.

Figure 2:
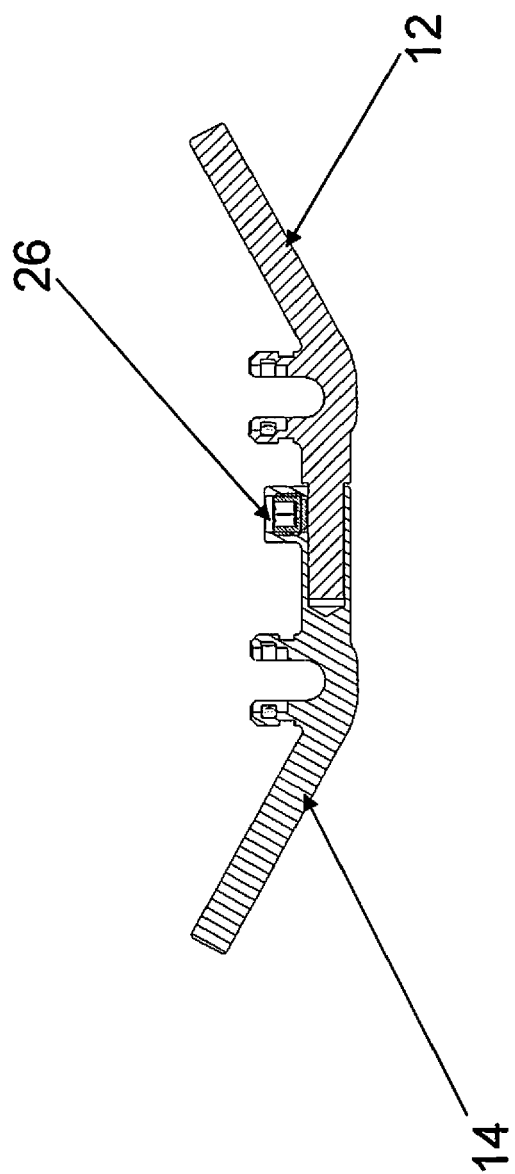
FIG. 2 illustrates a cross-sectional view of the iliac connector shown in FIG. 1.

The female portion 14 is also configured with a rod receiving element 22 for receiving a second elongated rod. The rod receiving element 22 is also configured to receive a locking cap for capturing and retaining a second elongated rod. The female portion 12 also includes a receiving portion 24 which is configured and adapted to receive the extension 18 of the male portion 12. The female portion 14 is also configured with a locking assembly 26 for locking the male portion 12 to the female portion 14. FIG. 2 illustrates the connector 10 fully assembled and in a locked position. The male portion 12 is adapted to fit within the female portion 14 of the connector 10, as illustrated. The locking assembly is then utilized to lock male portion 12 with the female portion 14. Although, FIGS. 1 and 2 illustrate on embodiment of the present invention, it should be noted that any type of connection assembly such as clamps, collets, and/or set screws may be used to lock the male portion 12 to the female portion 14.

Figure 3:
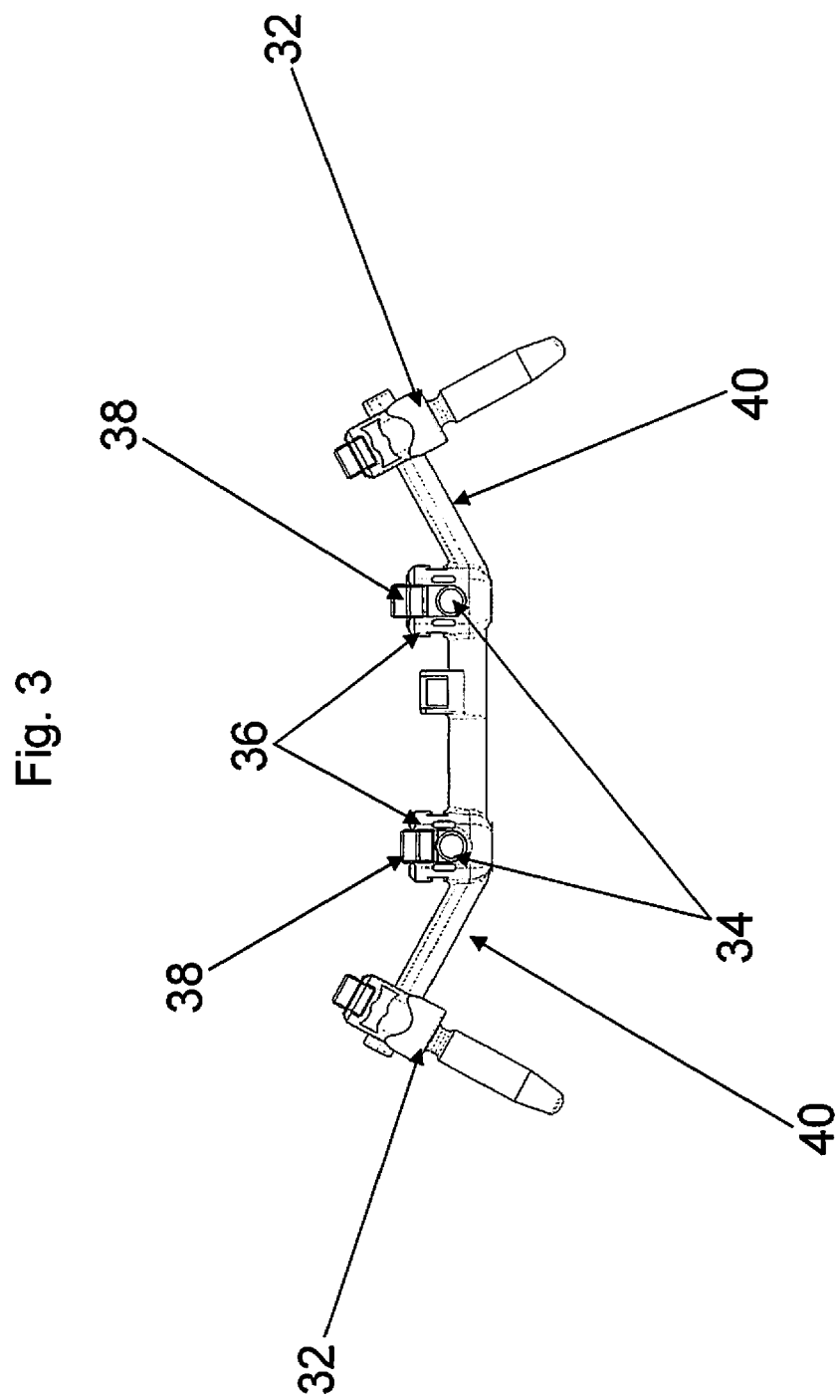
FIG. 3 illustrates a spine stabilization system according to the present invention.
Figure 4:
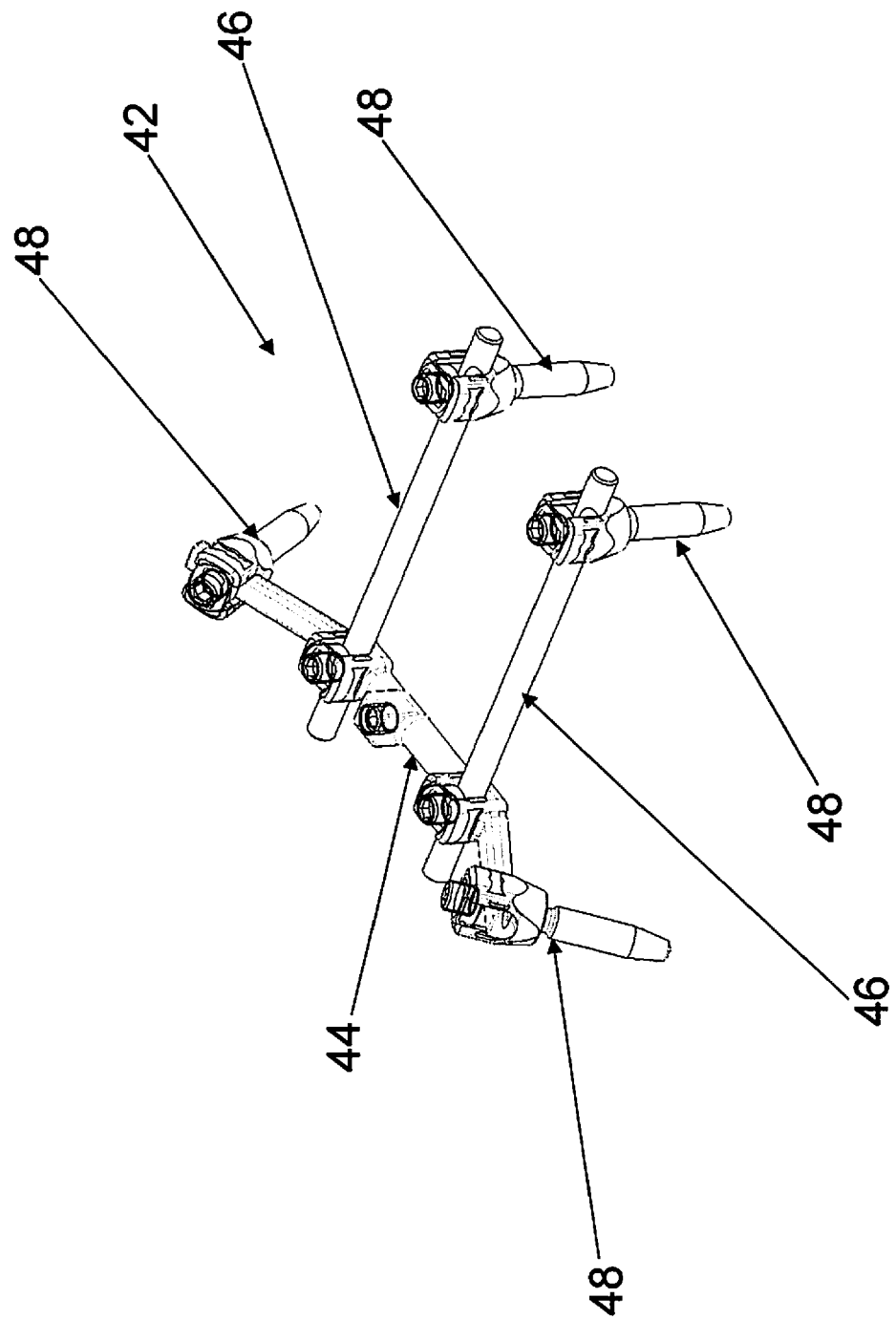
FIGS. 4 and 5 illustrate yet another spine stabilization system according to the present invention.
Figure 5:
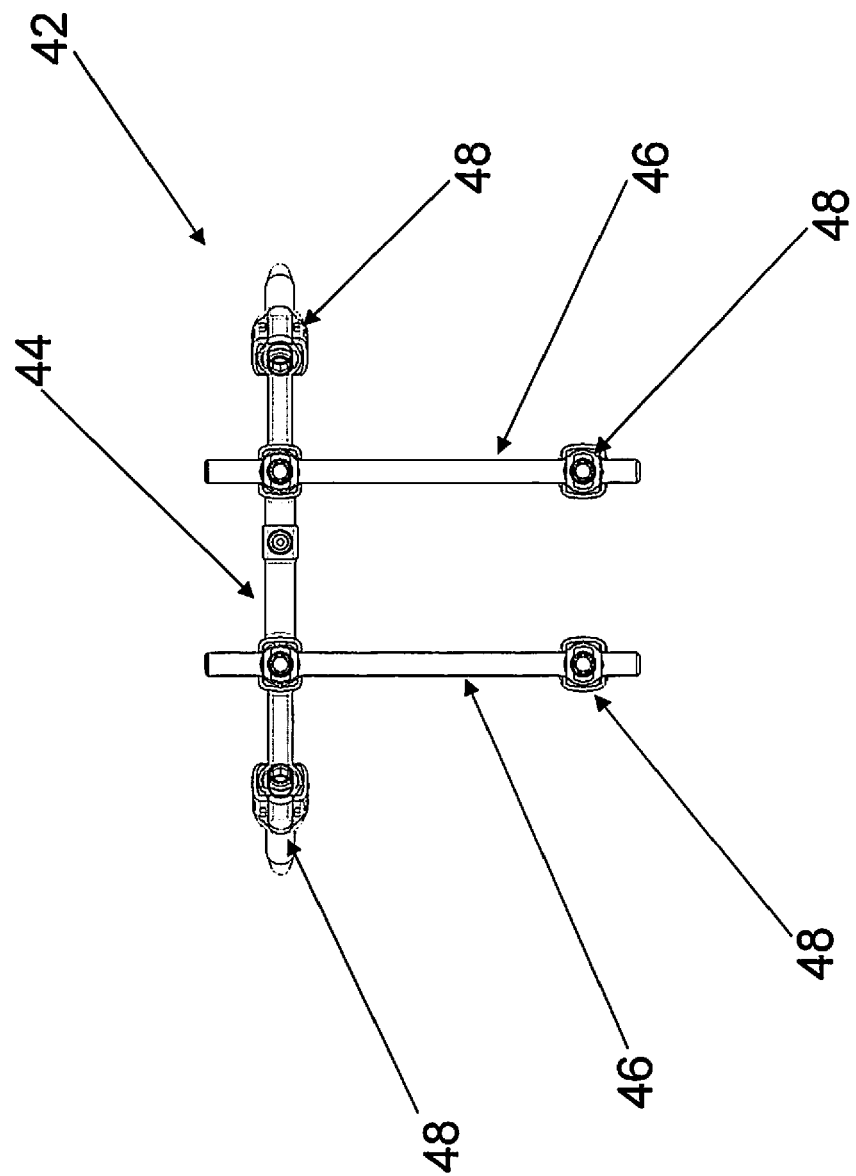

Now turning to FIGS. 3-5, it should be noted that the connector 30 is used in conjunction with bone screws to anchor into the Ilium. The connector 30 is adjustable in width and has rotational capabilities to aid in construct placement. As mentioned above, the connector 30 is adjustable laterally and rotationally and is locked in place with a set screw. Implantable rods 34 are placed into screw heads having rod receiving elements 36 such as tulips built into the connector 30 and locked in place with screw locking caps 38. Further construction is completed using rod/pedicle screw configurations. The connector 30 is able to provide solid anchorage in the sacro-iliac anatomy with a single implant that also acts as a cross connector. In addition, the attaching arms allow for superior stiffness and additional stability based upon the stiffness. It should be noted that the composition of the system may include titanium and stainless steel, however, the system is not limited to these materials. For example, any type of material such as plastic or PEEK may also be used.

In this system, the connector 30 is coupled to at least two bone anchors 32. The extension of the male portion 34 and the female portion 34 are coupled to each one of the bone anchors 32. Each bone anchor 32 is attached to the iliac crest thereby providing support across the sacrum of the spine. First, a bone anchor in inserted on both sections of the iliac crest. A surgeon generally accomplishes this task my measuring and calculating the position of the bone anchors based on the patient's anatomy and the dimensions of the cross connector required. Once the bone anchors are positioned, the male and female portion of the connector are attached and positioned within the tulips of the bone anchors. The connector is then adjusted and locked using the locking assembly of the connector. Then, the connector is locked into position within the tulips of the bone anchors.

FIGS. 4 and 5 illustrate a spinal stabilization system 42 according to the present invention. This system 42 includes a cross-connector 44, at least two elongated rods 46 and a plurality of bone anchors 48. This system 42 addresses the fusion and spinal fixation in the sacrum portion of the spine. The present fixation system is configured and dimensioned to span the iliac crest providing secure sacro-iliac fixation to enhance contact for spinal fusion. The present system utilizes bone screws 48 or anchors such as dual outer diameter screws to anchor the connector 44 in the anatomy laterally. A connection can then be made using the elongated rods 46 that can be positioned within the tulip heads of the bone screws 48. In addition the system 42 provides a structural base so that the connector acts as its own cross link to provide a "box" construction using a single implant. The connector 42 is adjustable medial/lateral to accommodate varying anatomic challenges. It should be noted that other configuration and adaptations of the connector with elongated rod and screws may be utilized to stabilize the spine. For instance, various angled rods and screws may be used to accommodate the anatomy of a patient's spine.

Example embodiments having the components of the present invention have been described herein. As noted, these example embodiments having been described for illustrative purposes only, and are not limiting. Other embodiments are possible and are covered by the invention. Such embodiments will be apparent to persons skilled in the relevant art based on the teachings contained herein. Thus, the breadth and scope of the present invention should not be limited by any of the above-described exemplary embodiments, but should be defined only in accordance with the following claims and their equivalents.

We claim:

1. A spine stabilization implant comprising:
   a first portion having a first fixed angulated extension, a first rod receiving element and a connecting element, wherein the first rod receiving element is monolithically formed with the first portion and the first fixed angulated extension, wherein the first fixed angulated extension has a first longitudinal axis and the connecting element has a central longitudinal axis, wherein the first longitudinal axis is at an angle relative to the central longitudinal axis, wherein the first fixed angulated extension is formed such that the angle is fixed and non-bendable; and
   a second portion having a second fixed angulated extension, a second rod receiving element, and a receiving portion for receiving the connecting element of the first portion, wherein the second fixed angulated extension has a second longitudinal axis and the receiving portion has a central longitudinal axis, wherein the connecting element is receivable and rotatable within the receiving portion;
   wherein the second portion is configured with a locking assembly for locking the first portion and second portion to one another,
   wherein the first rod receiving element and the second rod receiving element extend above the central longitudinal axis of the connecting element,
   wherein an opening of the first rod receiving element and an opening of the second rod receiving element each define a central axis,
   wherein the central axis of the first rod receiving element is positioned generally perpendicular to the central longitudinal axis of the connecting element,
   wherein the central axis of the second rod receiving element is positioned generally perpendicular to the central longitudinal axis of the receiving portion, and
   wherein a first elongate rod is received within the first rod receiving element above the central longitudinal axis of the connecting element and a second elongate rod is received within the second rod receiving element above the central longitudinal axis of the receiving portion.

2. The spine stabilization implant according to claim 1, wherein the locking assembly further comprises a set screw.

3. The spine stabilization implant according to claim 1, wherein the implant is comprised of titanium.

4. The spine stabilization implant according to claim 1, wherein the implant is comprised of PEEK.

5. The spine stabilization implant according to claim 1, wherein the locking assembly is a clamp.

6. A spine stabilization system comprising:
   a cross-connector comprising:
      a first portion with a first fixed angulated extension, a first rod receiving element and a connecting element, wherein the first rod receiving element is monolithically formed with the first portion and the first fixed angulated extension, wherein the first fixed angulated extension has a first longitudinal axis and the connecting element has a central longitudinal axis, wherein the first longitudinal axis is at an angle relative to the central longitudinal axis, wherein the first fixed angulated extension is formed such that the angle is fixed and non-bendable;
      a second portion having a second fixed angulated extension, a second rod receiving element, and a receiving portion, wherein the connecting element is receivable and rotatable within the receiving portion;
      wherein the second fixed angulated extension has a second longitudinal axis and the receiving portion has a central longitudinal axis,
      wherein the second portion is configured with a locking assembly for locking the first portion and second portion to one another,
   a first bone anchor coupled to the first fixed angulated extension and second bone anchor coupled to the second fixed angulated extension,
   wherein the first rod receiving element and the second rod receiving element extend above the central longitudinal axis of the connecting element,
   wherein an opening of the first rod receiving element and an opening of the second rod receiving element each define a central axis,
   wherein the central axis of the first rod receiving element is positioned generally perpendicular to the central longitudinal axis of the connecting element,
   wherein the central axis of the second rod receiving element is positioned generally perpendicular to the central longitudinal axis of the receiving portion, and
   wherein a first elongate rod is received within the first rod receiving element above the central longitudinal axis of the connecting element and a second elongate rod is received within the second rod receiving element above the central longitudinal axis of the receiving portion.

7. The spine stabilization system according to claim 6, wherein the locking assembly further comprises a set screw.

8. The spine stabilization system according to claim 6, wherein the cross-connector is comprised of titanium.

9. The spine stabilization system according to claim 6, wherein the cross-connector is comprised of PEEK.

10. The spine stabilization system according to claim 6, wherein the locking assembly is a clamp.

11. The spine stabilization system according to claim 6, wherein the first and second rod receiving elements comprise a first and second locking cap for retaining and capturing the first and second elongated rods.

* * * * *